(12) United States Patent
Das et al.

(10) Patent No.: US 6,385,509 B2
(45) Date of Patent: May 7, 2002

(54) TOOL ACTUATION AND FORCE FEEDBACK ON ROBOT-ASSISTED MICROSURGERY SYSTEM

(75) Inventors: Hari Das, Altadena; Tim R. Ohm, La Cresenta; Curtis D. Boswell, Pasadena; Robert D. Steele, Frazies Park, all of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/858,673

(22) Filed: May 15, 2001

Related U.S. Application Data

(63) Continuation of application No. 09/292,761, filed on Apr. 14, 1999, now Pat. No. 6,233,504.
(60) Provisional application No. 60/082,013, filed on Apr. 16, 1998.

(51) Int. Cl.$^7$ .............................................. G05B 15/00
(52) U.S. Cl. .................. 700/260; 700/245; 700/248; 700/257; 700/262; 700/263; 901/27; 901/28; 901/30; 901/34; 901/36; 600/595; 601/130; 341/20; 345/157; 345/161
(58) Field of Search .............................. 700/245, 248, 700/257, 260, 262, 263; 901/27, 28, 30, 34, 36; 600/595; 606/130; 341/20; 345/157, 161

(56) References Cited

U.S. PATENT DOCUMENTS

| | | | | |
|---|---|---|---|---|
| 3,923,166 A | * | 12/1975 | Fletcher et al. ................ | 414/4 |
| 4,905,001 A | * | 2/1990 | Penner ........................ | 341/20 |
| 5,184,319 A | * | 2/1993 | Kramer ......................... | 703/5 |
| 5,397,323 A | * | 3/1995 | Taylor et al. ............... | 606/130 |
| 5,625,576 A | * | 4/1997 | Massie et al. ................ | 703/6 |
| 5,709,219 A | * | 1/1998 | Chen et al. ................ | 600/595 |
| 5,710,870 A | | 1/1998 | Ohm et al. | |
| 5,731,804 A | * | 3/1998 | Rosenberg .................. | 345/156 |
| 5,784,542 A | | 7/1998 | Ohm et al. | |
| 5,898,599 A | * | 3/1999 | Massie et al. ............. | 345/161 |
| 5,945,978 A | * | 8/1999 | Holmes ....................... | 345/157 |
| 6,057,828 A | * | 5/2000 | Rosenberg et al. ......... | 345/156 |
| 6,184,868 B1 | * | 2/2001 | Shahoian et al. ........... | 345/161 |
| 2001/0018591 A1 | * | 8/2001 | Brock et al. ................ | 606/130 |

FOREIGN PATENT DOCUMENTS

| | | | |
|---|---|---|---|
| EP | WO 18925 | * | 4/1992 |
| WO | W O 01/18617 A1 | * | 3/2001 |

OTHER PUBLICATIONS

Kazerooni et al., The Dynamics and Control of a Haptic Interface Device, IEEE., pp. 453–464, 1994.*
Rosenberg et al., Perceptual Decomposition of Virgual Haptic Surface, IEEE., pp. 46–53, 1993.*
Koehn et al., Toward Evaluation of Shape Memory Alloy Actuators for Endosurgery, IEEE., pp. 1991–1996, 1995.*
Payandeh et al., Toward Design of a Modular Laparoscopic Assistant Stand (MLAS), IEEE., pp. 208–209, 1997.*

(List continued on next page.)

Primary Examiner—William A. Cuchlinski, Jr.
Assistant Examiner—McDieunel Marc
(74) Attorney, Agent, or Firm—Fish & Richardson P.C.

(57) ABSTRACT

An input control device with force sensors is configured to sense hand movements of a surgeon performing a robot-assisted microsurgery. The sensed hand movements actuate a mechanically decoupled robot manipulator. A microsurgical manipulator, attached to the robot manipulator, is activated to move small objects and perform microsurgical tasks. A force-feedback element coupled to the robot manipulator and the input control device provides the input control device with an amplified sense of touch in the microsurgical manipulator.

5 Claims, 8 Drawing Sheets

OTHER PUBLICATIONS

Hiemenz et al., A Physiologically Valid Simulator for Training Residents to Perform an Epidural Block, IEEE., pp. 170–173, 1996.*

Loly et al., Imposing Motion Constraints to a Force Reflecting Telerobot through Reall–Time Simulation of a Virtual Mechanism, IEEE., pp. 357–362, 1995.*

Reznik et al., Dynamic Simulation and Virtual Control of a Dformable Fingertip, IEEE., pp. 1669–1674, 1996.*

Morita et al., Design and Development of a new Robot Joint, IEEE., pp. 2469–2475, 1995.*

Forkey et al., A Comparison of Thumb And Foream Muscle Effort Required For Laparoscopic And Open Surgery Using AN Ergonomic Measurement Station, IEEE., pp. 17051708, 1997.*

Rosen et al., Force Controlled and Teleoperated Endoscopic Grasper For Minimally Invasive Surgery–Experimental Performance Evaluation, IEEE., pp. 1212–1221, 1999.*

Ali et al., Design Of Haptic Interface Throuth Stiffness Modulation For Endosurgery: Theory And Experiments, IEEE., pp. 1007–1012, 1998.*

Baumann et al., Haptic Interface for virtual reality based minimally invasive surgery simulation, 1998, IEEE, pp. 381–386.*

Tendick et al., Human machine interfaces for minimally invasive surgery, 1997, IEEE, pp. 2771–2776.*

Kwon et al., Haptic control of teh master hand controller for a microsurgical telerobot sytsem, 1999, IEEE, pp. 1722–1727.*

Benali et al., Design, control adn evaluation of a six DOF force feddback interface for virtual reality, 1999, IEEE, pp. 338–343.*

Astley et al., Design constraints for haptic surgery simulation, 2000, IEEE, pp. 2446–2451.*

Rosen et al., Markov modeling of minimally invasive surgery based on tool/tissue interaction and force/torque signatures for evaluating surgical skill, 2001, IEEE, pp. 579–591.*

* cited by examiner

TOOL ACTUATION AND FORCE FEEDBACK ON ROBOT-ASSISTED MICROSURGERY SYSTEM

CROSS-REFERENCE TO RELATED APPLICATIONS

This application is a continuation of U.S. patent application Ser. No. 09/292,761, filed Apr. 14, 1999 and issued as U.S. Pat. No. 6,233,504 on May 15, 2001, which claims benefit of the priority of U.S. Provisional Application Serial No. 60/082,013, filed Apr. 16, 1998 and entitled "A Tool Actuation and Force Feedback on Robot Assisted Microsurgery System."

ORIGIN OF INVENTION

The invention described herein was made in performance of work under a NASA contract, and is subject to the provisions of Public Law 96-517 (35 U.S.C. 202) in which the Contractor has elected to retain title.

BACKGROUND

The present specification generally relates to robotic devices and particularly to a mechanically decoupled six-degree-of-freedom tele-operated robot system.

Robotic devices are commonly used in factory-based environments to complete tasks such as placing parts, welding, spray painting, etc. These devices are used for a variety of tasks. Many of the robotic devices do not have completely mechanically-decoupled axes with passed actuation for transferring actuation through one joint in order to actuate another joint, without affecting the motion of any other joints. Also, the devices are large and bulky and cannot effectively perform small-scale tasks, such as microsurgical operations. In addition, these devices are not tendon-driven systems, and thus, do not have low backlash, which is desirable for microsurgical operations.

A decoupled six-degree-of-freedom robot system is disclosed in U.S. Pat. Nos. 5,710,870 and 5,784,542, issued to Ohm et al. The robot system has an input device functioning as a master to control a slave robot with passed actuation capabilities, high dexterity, six degrees-of-freedom with all six axes being completely mechanically decoupled, low inertia, low frictional aspect, and force-feedback capabilities.

The robot system, disclosed in the above-referenced patents, is a tendon-driven system without any backlash, and is therefore capable of precisely positioning surgical instruments for performing microsurgical operations.

SUMMARY

The inventors noticed, as a result of several simulated microsurgical operations, that the integration of a high precision micromanipulator with a highly sensitive force sensor to the slave robot can enhance the surgeon's feel of soft tissues. This allows effective performance of microsurgical tasks with resolution of the hand motion less than 10 microns. The force sensor readings are used to amplify forces with high resolution to an input device on the master control. The amplified forces allow the surgeon operating the master control handle to feel the soft tissues with greater sensitivity and to move the handle with exaggeration and precision. In addition, the push button switches mounted on the master control handle provides operator control of system enable and the micromanipulator.

In one aspect, the present disclosure involves robot-assisted tasks for use in microsurgery. An input control device with force sensors is configured to sense hand movements of an operator. The sensed hand movements actuate a mechanically decoupled robot manipulator. A microsurgical manipulator, attached to the robot manipulator, is activated to move small objects and perform microsurgical tasks. A force-feedback element coupled to the robot manipulator and the input control device provides the input control device with an amplified sense of touch in the microsurgical manipulator.

In some embodiments, the input control device has a handle with activation switches to enable or disable control of the robot manipulator. The activation switches also allow movement of the microsurgical manipulator.

In another aspect, a virtual reality system is disclosed. The virtual reality system includes a plurality of input control devices configured to sense operator body movements. Each device has a plurality of joints that are mechanically decoupled for transferring force sensed actuation through one joint in order to actuate another joint, without affecting the motion of any other joints. The operator body movements are translated into corresponding movements in a virtual reality environment. A plurality of force-feedback elements provides the input control devices with feedback of the senses created in the virtual reality environment.

In further aspect, a virtual augmentation system to a real-environment configuration is disclosed. The system includes a plurality of input control devices configured to sense operator body movements. Each device has a plurality of joints that are mechanically decoupled, where the operator body movements are translated into corresponding movements in a real environment with certain limitations placed on the movements by a virtual reality environment. A plurality of force-feedback elements provides the input control device with feedback of the senses created in the virtual reality environment to limit movements in the real environment.

In further aspect, a microsurgical training system is disclosed. The system includes a master input control device configured to sense operator body movements. The system also includes at least one force-feedback element coupled to the master input control device and at least one slave device coupled to the force-feedback element. The force-feedback element is configured to receive the operator body movements from the master input control device. The operator body movements of the master input control device are replicated in the slave device.

In one embodiment, a data collection and storage device is coupled to the master input control device. The data collection and storage device is used to collect and store the operator body movements for subsequent replay.

The details of one or more embodiments are set forth in the accompanying drawings and the description below. Other embodiments and advantages will become apparent from the following description and drawings, and from the claims.

BRIEF DESCRIPTION OF THE DRAWINGS

These and other aspects will be described in reference to the accompanying drawings wherein.

Like reference numbers and designations in the various drawings indicate like elements.

DETAILED DESCRIPTION

Micro-surgeons often use a microscope with 20 to 100 times magnification to help them visualize their microscopic work area. The microsurgical operations performed by these surgeons require manipulation of skin and tissue on the order of about 50 microns. A microsurgical manipulator, such as micro-forceps, can often scale down the surgeon's hand motions to less than 10 microns. This allows the average surgeon to perform at the level of the best surgeons with high levels of dexterity. In addition, the best surgeons will be able to perform surgical procedures beyond the capability of human hand dexterity. The integration of the high precision microsurgical manipulator with a highly sensitive force sensor to the slave robot enhances the surgeon's feel of soft tissues and allows effective performance of microsurgical tasks with resolution of the hand motion less than 10 microns.

The force sensor readings are used to amplify forces with high resolution to an input device on the master control. The amplified forces allow the surgeon operating the master control handle to feel the soft tissues with greater sensitivity and to move the handle with greater exaggeration and precision.

Figure 1:
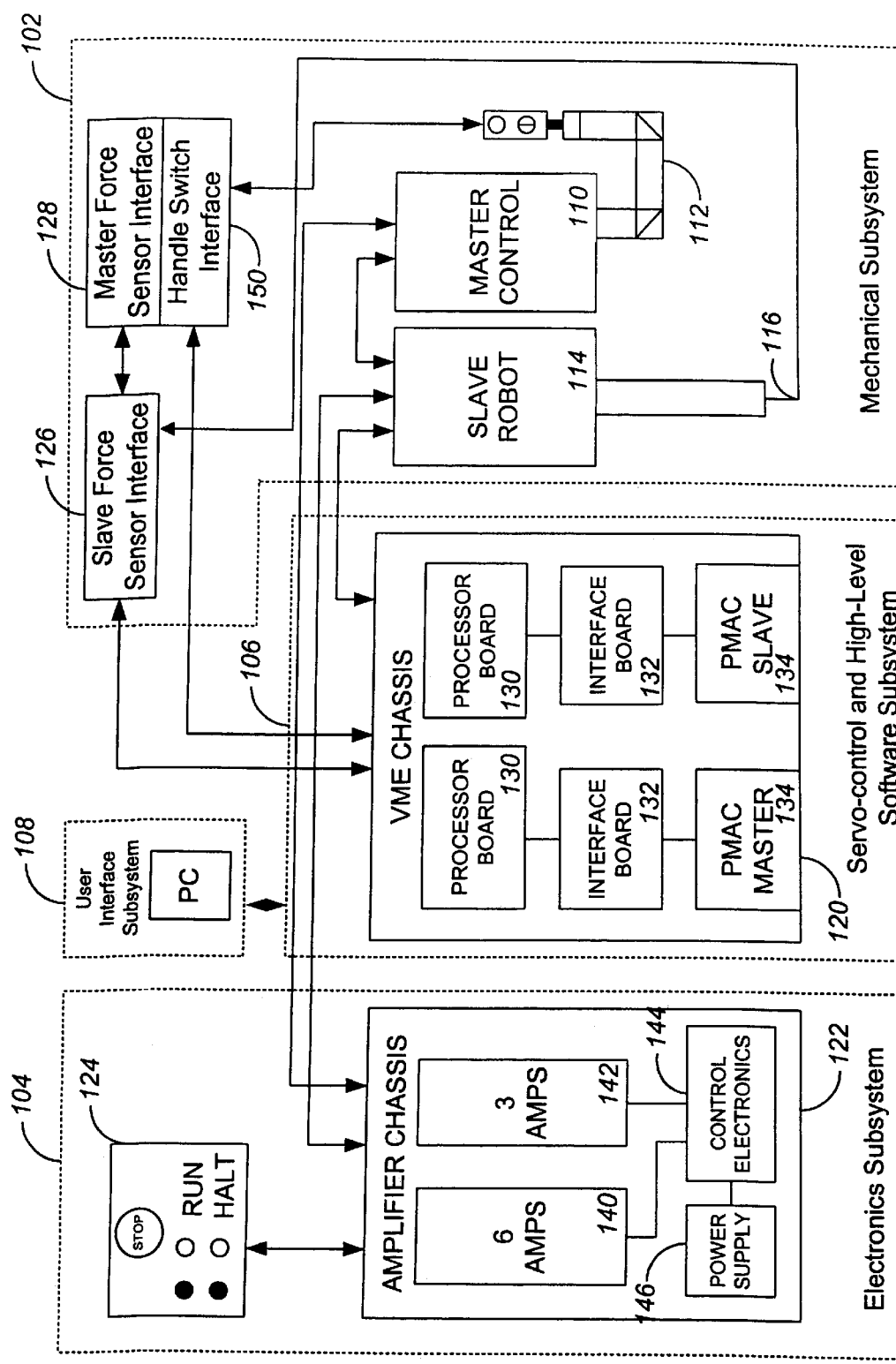
FIG. 1 is an overview block diagram of components of the robot-assisted microsurgery (RAMS) system.

FIG. 1 shows an overview block diagram of components of the robot-assisted microsurgery (RAMS) system. The components of the RAMS system have been categorized into four subsystems. They are the mechanical subsystem 102, the electronics subsystem 104, the servo-control and high-level software subsystem 106 and the user interface subsystem 108.

The mechanical subsystem 102 includes a master control system 110 with an input device 112 and a slave robot arm 114 with associated motors, encoders, gears, cables, pulleys and linkages that cause the tip 116 of the slave robot to move under computer control and to measure the surgeon's hand motions precisely. The subsystem 102 also includes slave and master force sensor interfaces 126, 128, and a master input device handle switch interface 150.

The electronics subsystem 104 ensures that a number of error conditions are handled gracefully. Components of the electronics subsystem 104 are a Versa Module EuroCard (VME) chassis 120, an amplifier chassis 122 and safety electronics 124.

The VME chassis 120 contains VME processor boards 130 used for high-level system control. The VME chassis 120 also contains two sets of Programmable Multi-Axis Controller (PMAC) servo-control cards 134, power supplies, and two cable interface boards 132.

The amplifier chassis 122 contains the six slave robot motor drive amplifiers 140 and three master control device motor drive amplifiers 142. The amplifier chassis 122 also includes a system control electronics board 144 and an amplifier power supply 146.

The safety control electronics 124 includes the control electronics board and brake relay board. The purpose of the braking function is to hold the motors in place when they are not under amplifier control. Programmable logic devices (PLDs) in the safety control electronics module 124 monitors amplifier power, operator control buttons and the HALT button, and a watchdog signal from the high-level software and control processor. Any anomaly triggers brakes to be set on the slave robot joint and a fault LED to be lighted. The operator must reset the safety control electronics to re-activate the system.

The servo-control and high-level software subsystem 106 is implemented in hardware and software. The subsystem 106 includes servo-control boards 134 and the computational processor boards 130. Servo-control software functions include setting-up the control parameters and running the servo-loop on the servo-control boards 134 to control the six motors, implementing the communication between the computation and servo-control boards 134, initializing the servo-control system and communicating with the electronics subsystem 104 and the user interface subsystem 108.

The user interface subsystem 108 interfaces with a user, controls initialization of the system software and hardware, implements a number of demonstration modes of robot control and computes both the forward and inverse kinematics.

In one embodiment of the subsystem 108, the user specifies the control modes of the system through a graphic user interface (GUI) implemented on a computer system, such as a personal computer (PC) or a workstation. Commands entered into the GUI are transmitted over an Ethernet connection or by a serial interface and are received on the real-time software side of the system.

Figure 2:
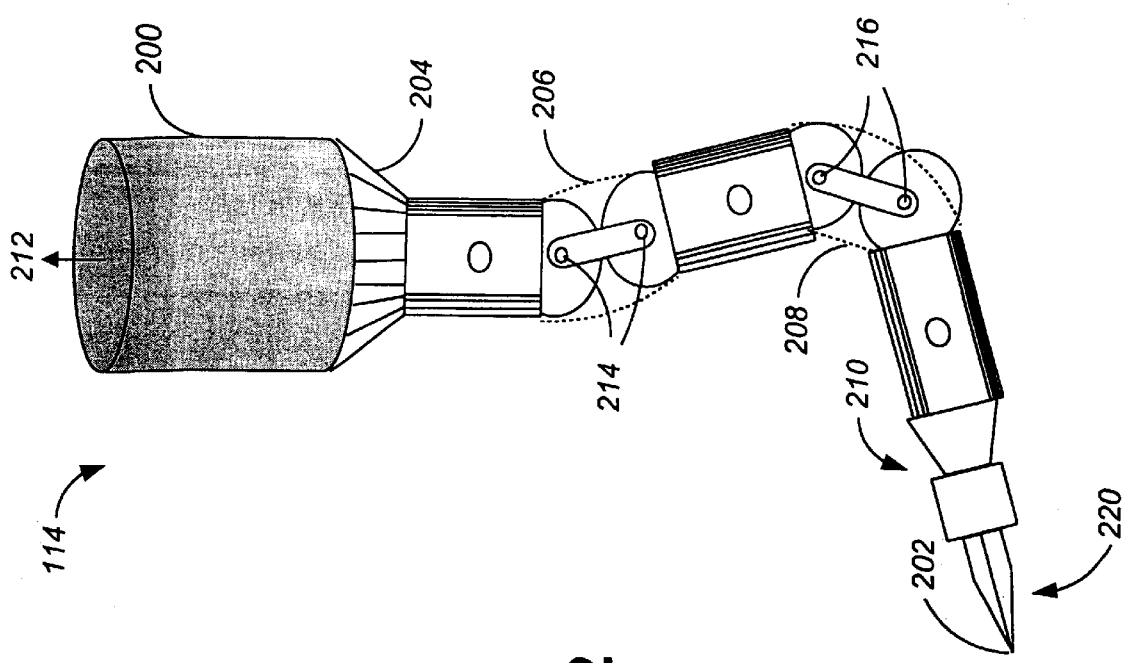
FIG. 2 is a perspective view of a slave robot arm.

FIG. 2 shows the slave robot arm 114. The arm 114 is a six degrees-of-freedom tendon-driven robotic arm designed to be compact yet exhibit very precise relative positioning capability as well as maintain a very high work volume. Physically, the arm measures 2.5 cm in diameter and is 25 cm long from its base 200 to the tip 202. The arm 114 is mounted to a cylindrical base housing 200 that measures 12 cm in diameter by 18 cm long that contains all of the drives that actuate the arm.

The joints of the arm 114 include a torso joint 204, a shoulder joint 206, an elbow joint 208, and a wrist joint 210. The torso joint 204 rotates about an axis aligned with the base axis 212 and positioned at the point the arm 114 emerges from its base 200. The shoulder joint 206 rotates about two axes 214 that are in the same plane and perpendicular to the preceding links. The elbow joint 206 also rotates about two axes 216 that are in the same plane and perpendicular to the preceding links. The wrist joint 210 makes three-axes rotations called pitch, yaw and roll rotations.

The slave wrist 210 design utilizes a dual universal joint to give a three degrees-of-freedom, singularity free, mechanically decoupled joint that operates in a full hemisphere of motion. The master wrist 210 design uses a universal joint to transmit rotation motion through the joint while allowing pitch and yaw motions about the joint resulting in singularity free motion over a smaller range of motion in three degrees-of-freedom.

Figure 3:
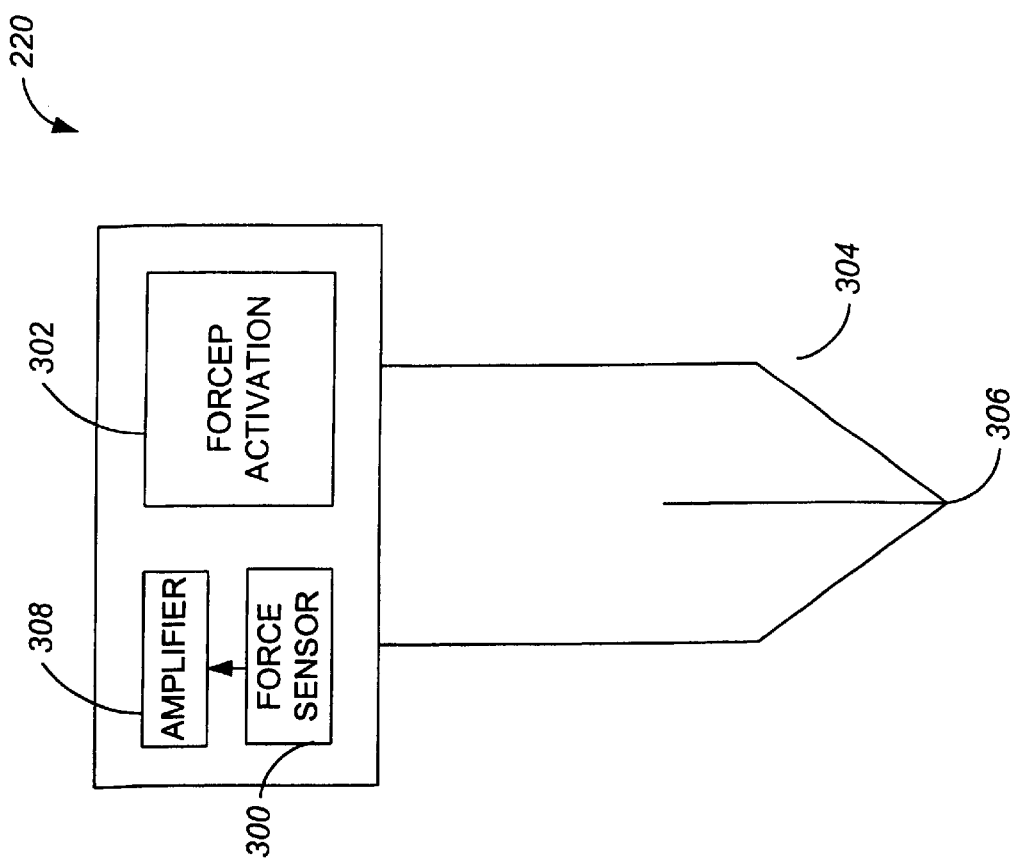
FIG. 3 is one embodiment of the end effector of the slave robot arm.

FIG. 3 shows one embodiment of the end effector 220 of the slave robot. The end effector 220 is force sensor instrumented micro-forceps 304 actuated by a miniature DC motor 302. Simultaneous sensing of force interactions at the robot tip 306 and manipulation with the forceps 304 is possible with the end effector 220. Force interactions measured with the force sensor 300 are amplified, processed and used to drive the master arm to amplify the sense of touch at the master handle by an amplifier 308.

Figure 4:
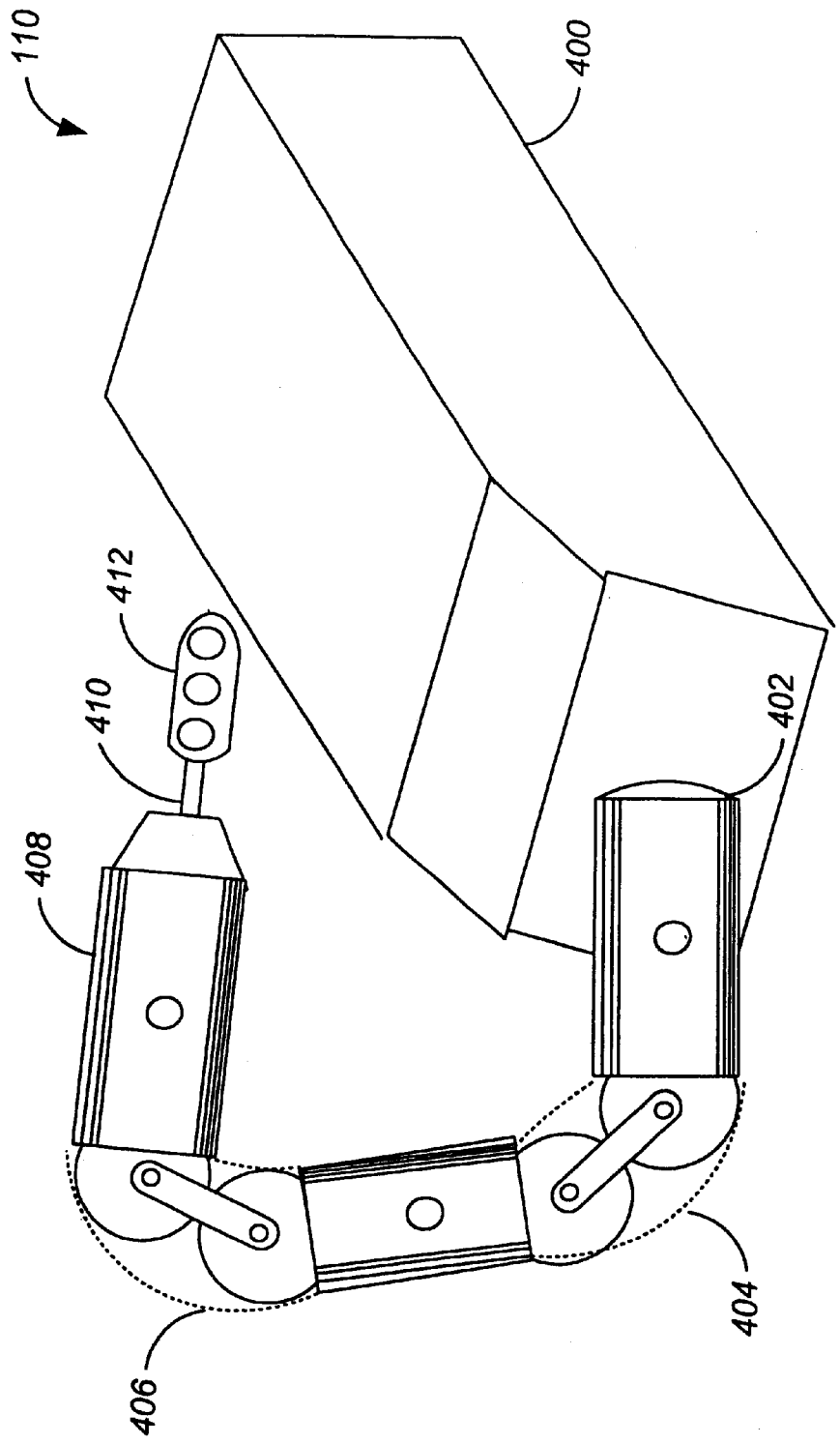
FIG. 4 is a perspective view of a master control device.

FIG. 4 shows a master control device 110 similar to the slave robot 114. The device 110 also has six tendon-driven joints. The master control device 110 is 2.5 cm in diameter and 25 cm long. The base 400 of the master control device 110 houses high-resolution optical encoders for position sensing. Since the smallest incremental movement during microsurgery is about 10 microns, 10 encoder counts is the minimum desirable incremental movement. As a result, one encoder count corresponds to one-micron movement at the tip of the end effector 306. High-resolution encoders are necessary for reducing the amount of gearing necessary to achieve the required positional resolution while limiting friction.

In addition, the base 400 preferably includes three arm motors and three wrist motors to create the force-feedback capability on the torso 402, shoulder 404, and elbow 406 axes, and the three-axis wrist 408, respectively. The wrist 408 is coupled to a six-axis force sensor 410 that is coupled to a handle 412.

Figure 5:
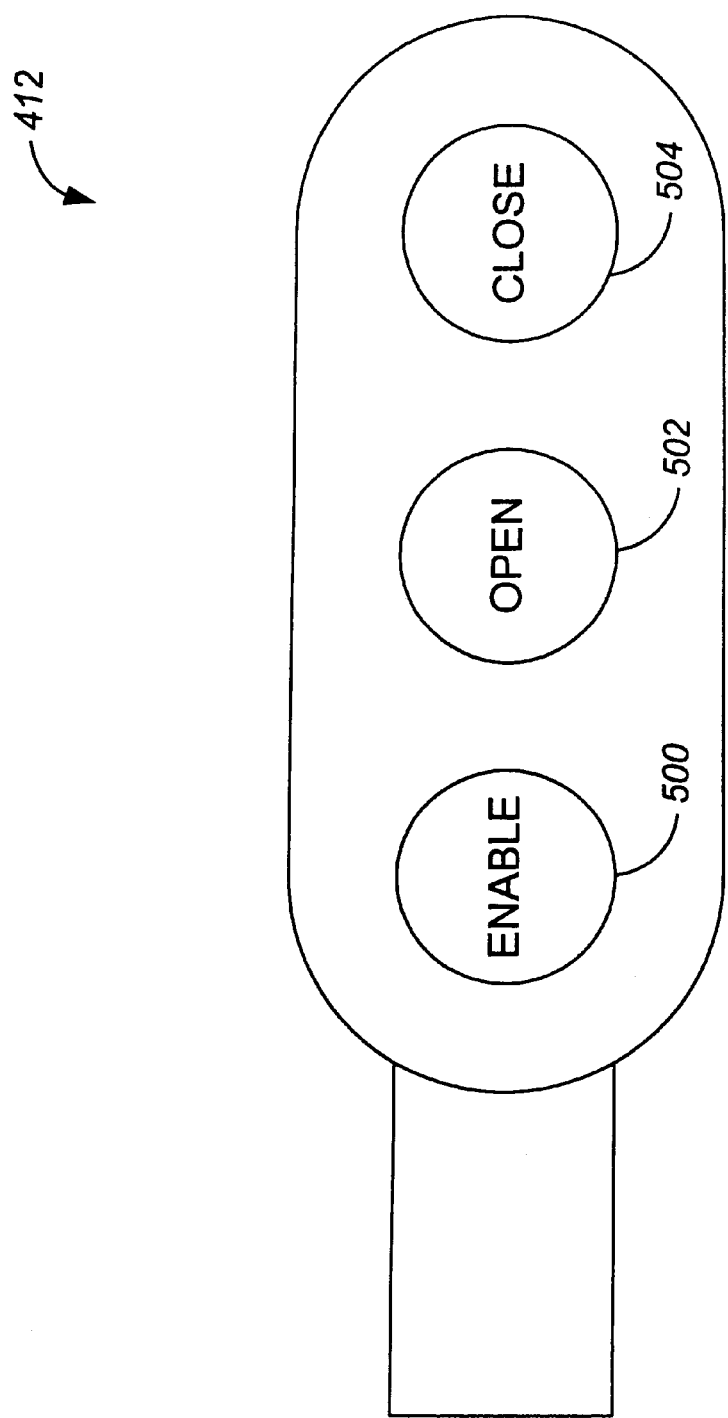
FIG. 5 is a front view of a master control device handle.

FIG. 5 shows the master control device handle 412. There are three push button switches mounted on the handle 412 which provide operator control of the system and the opening and closing of the micro-forceps 304 on the slave robot arm 220. The enable switch 500 enables operator control of the system. The open switch 502 and the close switch 504 control the microsurgical manipulator 304 at the tip of the end effector 306 by opening and closing the micro-forceps 304, respectively.

Figure 6:
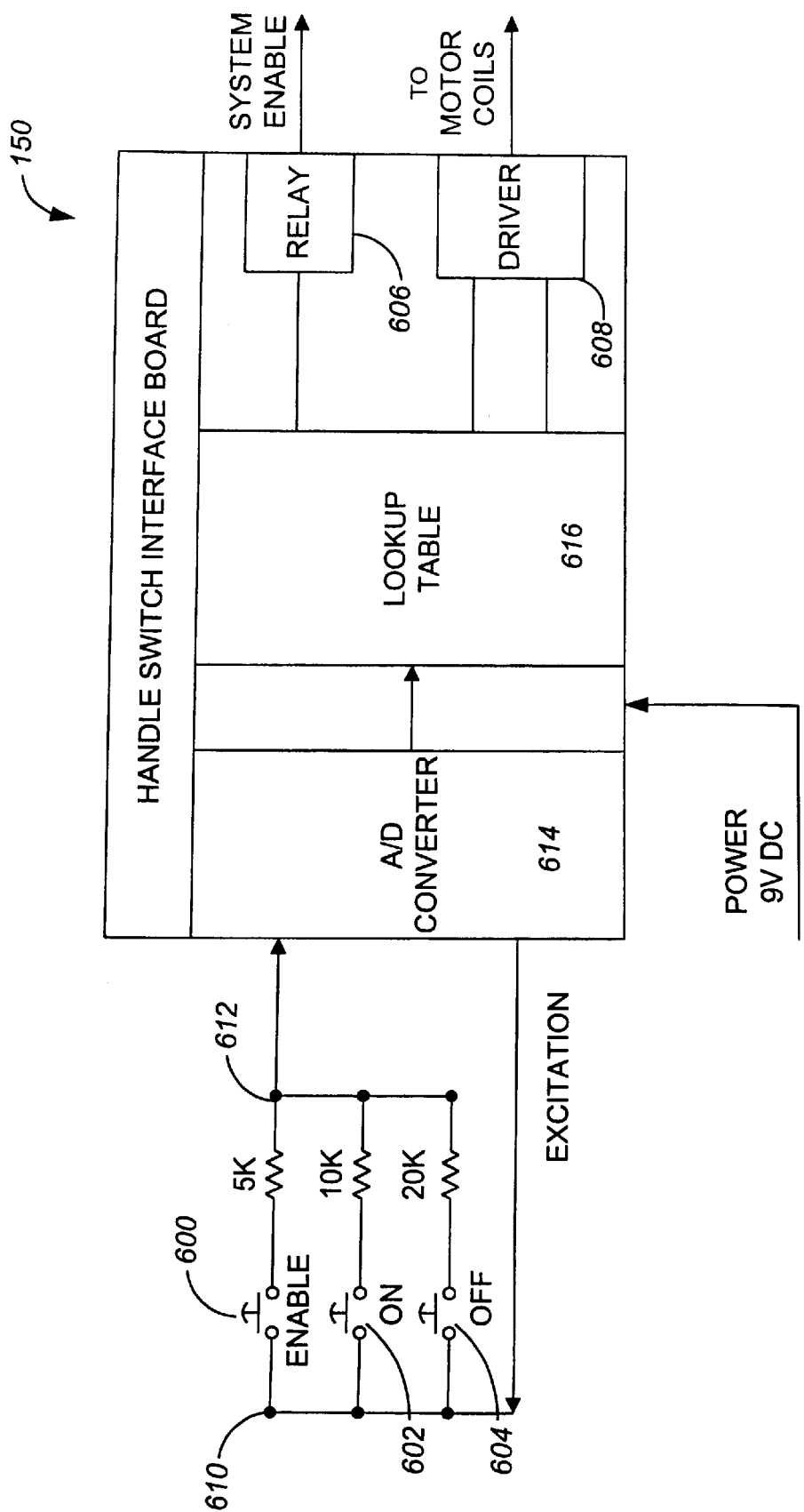
FIG. 6 is a block diagram of a master handle switch interface board.

FIG. 6 shows a block diagram of a master handle switch interface board 150. One switch 600 is used to inform the system computer that slave motion should be enabled. The output circuit is a relay 606 that turns system enable on or off. The other two switches 602, 604 are used to cause the slave robot manipulator 304 to move in with one switch and out with the other and no motion if both or neither are activated.

The switches 600, 602, 604 each have a resistor in series with its contacts. All switch-resistor pairs are connected in parallel providing a two-terminal switch sensor circuit connecting the nodes 610 and 612. The resistors are selected with different weighting values so that each switch has a different effect on the total resistance of the switch sensor. The switch sensor circuit is one element in a two-element voltage divider network. When different switches and combinations of switches are activated the voltage divider output changes.

The voltage divider network output changes are measured by a 7-bit analog-to-digital converter (ADC) 614. The numbers generated by the ADC output reflect the condition of the switches that are activated. The ADC numbers are decoded into eight discrete ranges using a lookup table 616. The states are modified in the decode logic to eliminate unwanted conditions. For example, both motor direction activated will cause no motor action.

The enable output circuit is a single-pole-double-throw relay 606 whose contacts are wired to an input port on the main computer. The motor driver output has two bipolar drivers 608 that can drive the motor in either direction or not at all.

Figure 7:
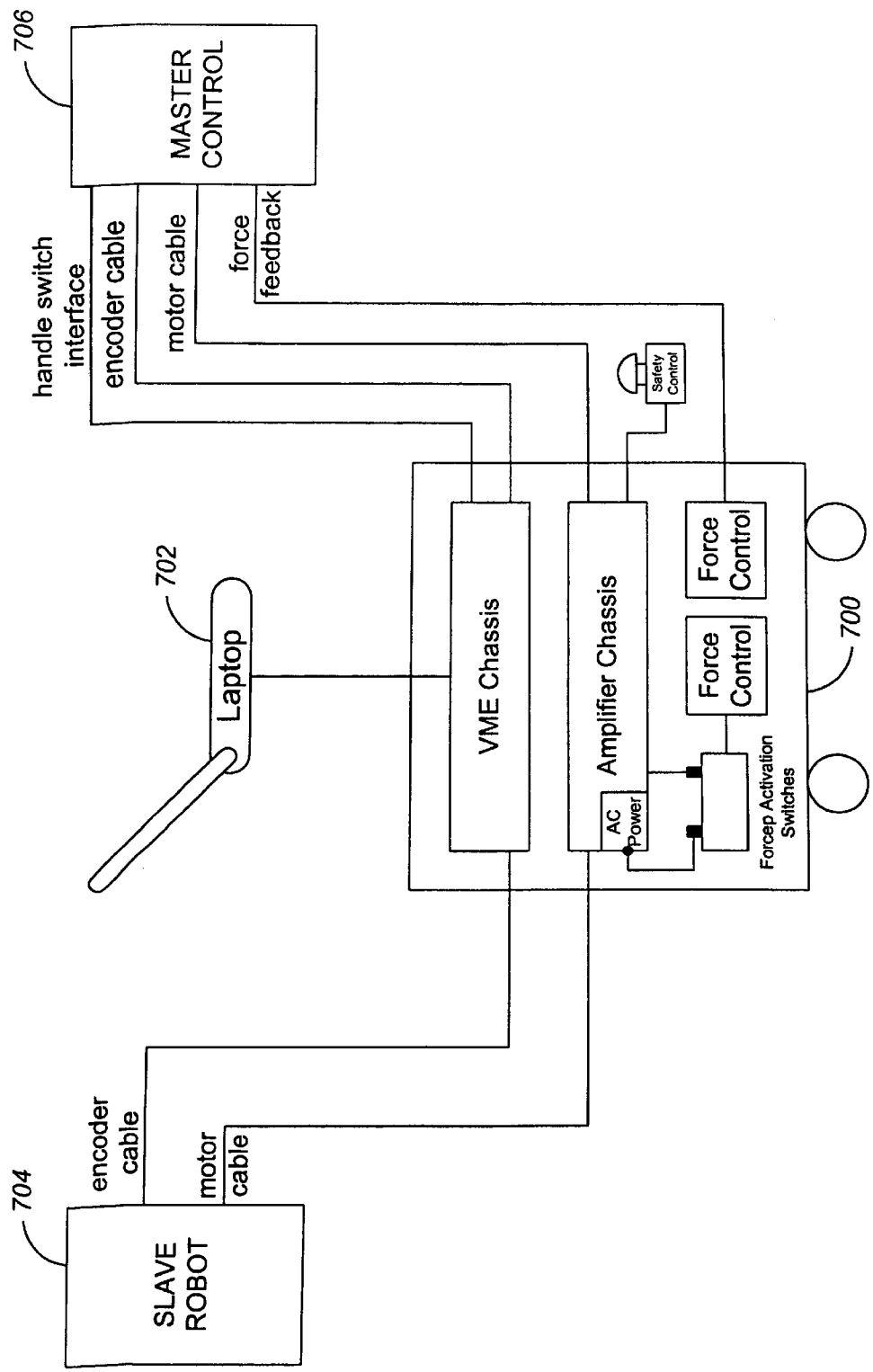
FIG. 7 is one embodiment of the RAMS system illustrating the advantages of compact size and lightweight.

FIG. 7 shows one embodiment of the RAMS system. The figure illustrates the advantages of compact size and lightweight. The entire electronics and servo-control subsystems containing the VME chassis, the amplifier chassis and the force-control boards are installed on a movable rack 700. A computer, such as a laptop 702, can be placed on top of the rack 700. The slave robot 704 and the master control device 706 can be placed around an operating table with interface cables connecting them to the rack 700.

Other advantages of the RAMS system include easy manipulation of the slave robot arm and manipulator, large work envelope, decoupled joints, low backlash, and low stiction.

The slave robot arm and manipulator can be easily maneuvered using the master input device handle and the push-button switches. The switch operated indexed motion allows the surgeon to efficiently control the robot arm and manipulator.

The RAMS system provides a large work envelope because each joint of the slave robot arm 114 has a large range of motion. The torso has 165 degrees of motion while both the shoulder and elbow have a full 360 degrees of motion. This high range of motion is attained by the double-jointed scheme. The wrist design has 180 degrees of pitch and yaw with 540 degrees of roll. Such large motion ranges increases the work volume and reduces the chance of a joint reaching a limit during operation.

The mechanically decoupled slave and master arm joints of the RAMS system simplifies kinematic computations. Furthermore, mechanically decoupled joints provide partial functionality even with one joint failure.

The RAMS system provides low backlash by using dual drive trains that are pre-loaded relative to one another. Low backlash is essential for doing fine manipulations. Five of the six degrees-of-freedom have zero backlash and the sixth, which is a result of the wrist design, has low backlash.

The RAMS system also provides low stiction with an incorporation of precision ball bearings in every rotating location of the robot. This reduces metal-to-metal sliding and minimizes stiction. Low stiction is effective in providing small incremental movements without overshooting or instability.

Figure 8:
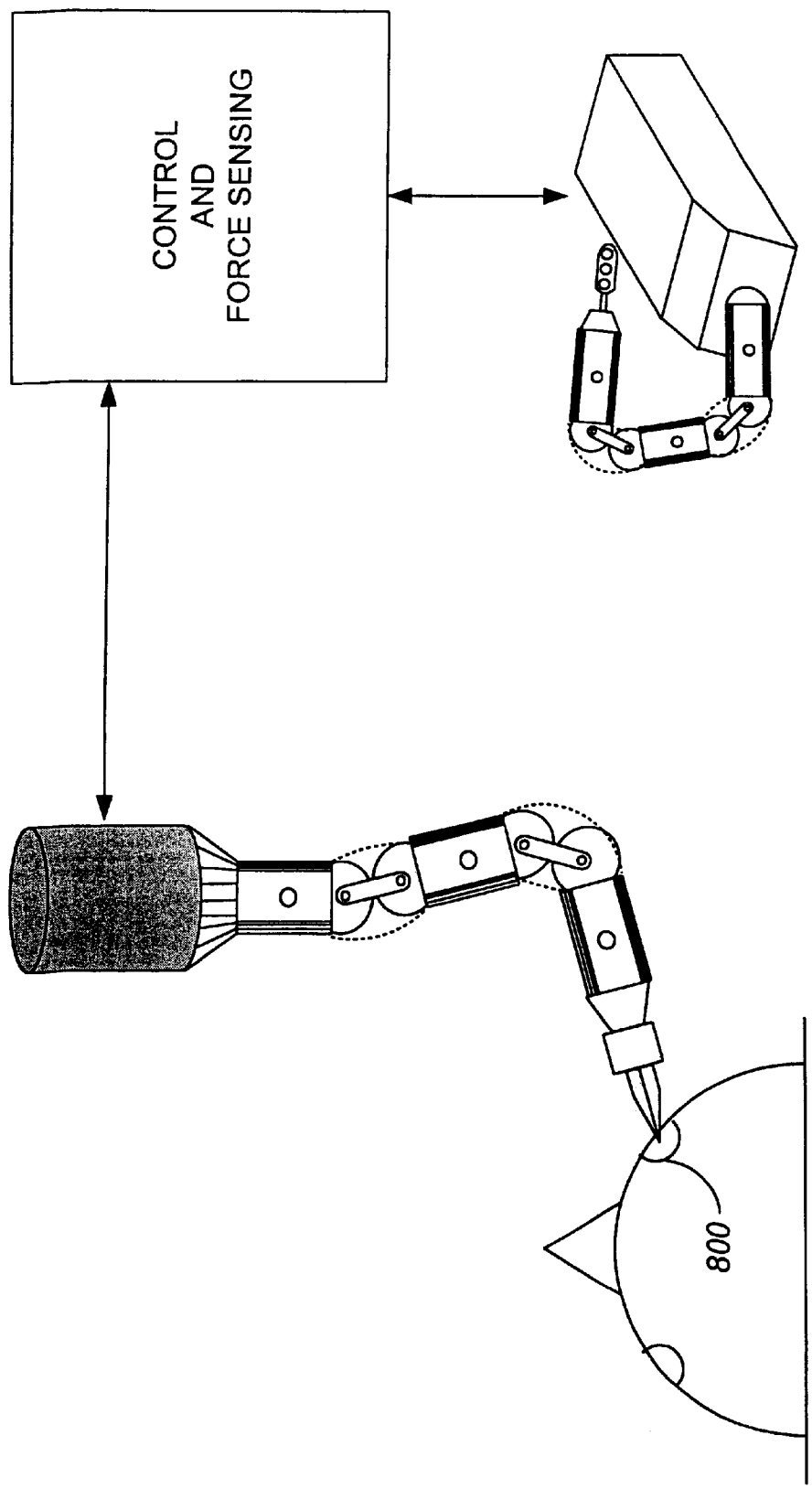
FIG. 8 illustrates a simulated eye microsurgery procedure using the RAMS system.

FIG. 8 illustrates a simulated eye microsurgery procedure successfully conducted using the RAMS system. The procedure demonstrated was the removal of a microscopic 0.015-inch diameter particle from a simulated eyeball 800.

The RAMS system was demonstrated in other procedures, including a dual-arm suturing procedure. Two RAMS systems were configured as left and right arms to successfully perform a nylon suture to close a 1.5 mm long puncture in a thin sheet of latex rubber.

The RAMS system can be used in many other applications such as a haptic device in virtual reality (VR) system, synthetic fixtures or virtual augmentation to the real environment, a simulator to train for microsurgical procedures, and a data collection system for measuring the hand motions made by an operator.

Although the RAMS system was not developed as a VR system, components of the RAMS system are applicable in the VR system. In one application, the master control arm is a unique haptic device that presents virtual or real force interaction to the user related to touch perception and feedback. The master control arms' ability to measure hand motions to less than 10 microns in translation and to 0.07 degrees in orientation and its pencil grasp make it ideal as an interface for positioning and feeling of a probe in a virtual environment.

In another application, the synthetic fixtures or virtual augmentation to the real environment is implemented on the RAMS system to assist the user in performing complex tasks. For example, in the eye surgery procedure, constraints on the motion of the slave robot are implemented to allow the surgical instrument mounted on the slave robot to pivot freely about the entry point in the eyeball. Activation of this mode causes loss of user control in two degrees of freedom of the slave robot. The automated control system prevents motion that moves the instrument against the eyeball wall.

In another application, the user interface part of the RAMS system can be used as a simulator to train for microsurgical procedures. Expert guidance to a novice surgeon can be implemented by replicating the expert motions of a master device on a similar device held by the novice.

In further application, the RAMS system also can be used as a data collection system for measuring the hand motions made by an operator of the system. This data is useful for characterizing the performance of the user. Much may be learned from analysis and characterization of the collected data including evaluation of the potential microsurgical abilities of surgical residents, prediction of the skill-level of a surgeon at any time or providing some insight into the nature of highly skilled manual dexterity.

Although only a few embodiments have been described in detail above, those of ordinary skill in the art certainly understand that modifications are possible. For example, as an alternative to constraining the motion of the slave robot in microsurgery procedure, forces can be simulated on the master handle that would guide the user into making safe motions. All such modifications are intended to be encompassed within the following claims, in which:

What is claimed is:

1. A microsurgery system, comprising:

a robot manipulator having a plurality of mechanically decoupled joints, said plurality of mechanically decoupled joints allowing actuation of a joint without affecting motion of any other joints;

an effector coupled to said robot manipulator to apply a force to an object; and a force feedback element adapted to amplify a return force from said effector.

2. The system of claim 1, further comprising:

master control system coupled to said robot manipulator, said master control system allowing an operator to input hand movement, where said hand movement is converted into amount of force applied at the effector.

3. The system of claim 1, wherein the return force of said force feedback element provides an exaggerated sense of feel, such that said sense of feel allows an operator to feel smaller force feedback than that without said force feedback element.

4. A method of performing a microsurgery, comprising:

converting operator hand movements into a series of forces to be applied by a manipulator;

determining a series of manipulator movements, said movements performed by a combination of manipulator joint movements;

actuating the manipulator joint movements;

providing an amplified feedback of a return force felt by said manipulator.

5. The method of claim 4, wherein said actuating includes providing movement of each joints in a mechanically decoupled orientation such that a joint movement is made without affecting movement of any other joints.

* * * * *